United States Patent [19]

Chamberlain

[11] Patent Number: 5,529,975

[45] Date of Patent: Jun. 25, 1996

[54] SPRAYABLE AGRICULTURAL COMPOSITIONS

[75] Inventor: Peter Chamberlain, West Yorkshire, England

[73] Assignee: Allied Colloids Limited, England

[21] Appl. No.: 301,629

[22] Filed: Sep. 7, 1994

Related U.S. Application Data

[63] Continuation-in-part of Ser. No. 927,411, Oct. 23, 1992, abandoned, and a continuation-in-part of Ser. No. 65,047, May 24, 1993, which is a continuation of Ser. No. 857,258, Mar. 25, 1992, abandoned.

[30] Foreign Application Priority Data

Mar. 26, 1990 [GB] United Kingdom ............... 9006676
Mar. 26, 1991 [GB] United Kingdom ............... 9106409

[51] Int. Cl.$^6$ .................... A01N 33/04; A01N 25/00; A01N 57/04
[52] U.S. Cl. .................... 504/116; 504/206; 504/235; 504/244; 504/345; 71/DIG. 1
[58] Field of Search .................... 504/116, 206, 504/235, 244, 345; 71/DIG. 1

[56] References Cited

U.S. PATENT DOCUMENTS

| | | | |
|---|---|---|---|
| 3,360,356 | 12/1967 | Vartiak | 71/65 |
| 3,813,345 | 5/1974 | Urton | 252/312 |
| 4,126,443 | 11/1978 | Gadea | 504/280 |
| 4,657,581 | 4/1987 | Takematsu et al. | 504/336 |
| 5,037,654 | 8/1991 | Puritch et al. | 424/405 |

FOREIGN PATENT DOCUMENTS

| | | |
|---|---|---|
| 785706 | 5/1968 | Canada . |
| 1023264 | 12/1977 | Canada . |
| 0055857 | 7/1982 | European Pat. Off. . |
| 0245970 | 11/1987 | European Pat. Off. . |
| 0365279 | 4/1990 | European Pat. Off. . |
| 0376910 | 7/1990 | European Pat. Off. . |
| 1285930 | 1/1962 | France . |
| 58-72501 | 4/1983 | Japan . |
| 61-78701 | 4/1986 | Japan . |
| 831344 | 3/1960 | United Kingdom . |
| 1506568 | 4/1978 | United Kingdom . |
| 2107986 | 5/1983 | United Kingdom . |
| WO88/10069 | 12/1988 | WIPO . |
| WO89/03175 | 4/1989 | WIPO . |

OTHER PUBLICATIONS

A, Sundaram, Effect of a Nalco–trol ll on Bioavailability of Glyphosate in Laboratory Trials, J. Environ. Sci. Health, vol. 25, No. 3, 309–332 (1990).

*Primary Examiner*—Richard L. Raymond
*Assistant Examiner*—Brian C. Bembenick
*Attorney, Agent, or Firm*—Dickstein, Shapiro & Morin

[57] ABSTRACT

The systemic activity of systemic active ingredients in sprayed foliar systemic compositions is improved by incorporating water soluble polyacrylamide in the sprayed composition. The polyacrylamide can have a molecular weight sufficiently low that its presence does not substantially affect the spray pattern of the composition, and the polyacrylamide can have low solution viscosity such that a convenient concentrate can comprise an aqueous solution of the active ingredient and the polymer. Alternatively, the polymer can be supplied as a powder or as a reverse phase emulsion or dispersion. The sprayable composition is preferably formulated such that the spray droplets have a small particle size.

13 Claims, No Drawings

SPRAYABLE AGRICULTURAL COMPOSITIONS

RELATED APPLICATIONS

This application is a continuation-in-part of Ser. No. 07/927,411 of 23rd Oct. 1992 (abandoned) which originated as WO91/14365 of 26th Mar. 1990 and is a continuation-in-part of Ser. No. 08/065,047 filed 24th May 1993 (pending) which was a continuation of Ser. No. 07/857,258 filed 25th Mar. 1992, (abandoned) all by Peter Chamberlain.

FIELD OF THE INVENTION

This invention relates to foliar systemic compositions, that is to say compositions that are to be sprayed on to plants to administer an agriculturally useful active ingredient that is absorbed through the leaves and into the plant so as subsequently to achieve systemically an agriculturally useful effect such as a herbicidal, fungicidal, insecticidal or plant growth regulatory effect. In particular, the invention relates to sprayable compositions and to concentrates from which they can be obtained.

DESCRIPTION OF THE PRIOR ART

Agriculturally active ingredients are often provided to the user as a concentrate, which the user can then dilute to form an aqueous sprayable composition. Many forms of agricultural concentrates are known and these consist of the active ingredient and a carrier, that can include various components. It is known to include polymeric material as part of the carrier in some agricultural concentrates.

When the concentrate is a solution in water or organic solvent, it is very rare to include polymeric material. However when the concentrate is a dispersion in water it is common to include a small amount of polymeric thickener and when the concentrate is a dispersible grain it is common to include a small amount of polymeric binder. A wide variety of polymers have been mentioned in the literature as thickeners and binders (for instance the cellulosic, acrylamide, vinyl alcohol and other polymers proposed in U.S. Pat. No. 4,657,781) but in practice very few polymers have been used. For instance the thickener is almost always xanthan gum. The thickeners and binders used in agricultural concentrates generally have high molecular weight, in order that they can impart the desired thickening or binding effect. They are generally present in a minor amount relative to the active ingredient, for instance less than 0.1 parts polymer per part by weight active ingredient.

In U.S. Pat. No. 4,126,443 a very small amount of low molecular weight hydrolysed acrylamide is incorporated into an aqueous concentrate of a particular herbicide in order to prevent crystallisation within the concentrate.

The polymer is formed of 50 to 99% acrylic acid groups 1 to 50% acrylamide groups and is present in the concentrate in an amount that is recommended to be below 640 ppm (0.064%) although in one example the amount is 0.5%. The amount of active ingredient in the concentrate is from 20 to 40% and so when this is diluted to form asprayable composition the concentration of polymer in the sprayable composition will be only a few parts per million.

It is also known to include polymers in the agricultural composition that is to be applied, so as to modify the properties of that composition. For instance in EP-A-55857 a particular carbamate insecticide is blended with an excess of various film-forming polymers and applied as a film from an ethanol solution, and it is suggested that the effect of the polymer is to alter the crystallisation properties of the carbamate when the solvent evaporates and a film is formed. There is no suggestion the solution should be sprayed and the carbamate is not a foliar systemic active ingredient. Indeed the teaching in this patent (to adjust the crystallisation properties) is clearly unrelated to systemic activity which requires absorption of the active ingredient, presumably while still in the liquid phase, through the leaves into the plant. The preferred polymers in EP 55857 are said to be water soluble cellulose derivatives but polyacrylamides, ethylene oxide resins and water insoluble polyamides, esters and other polymers are mentioned including very high molecular weight polyethylene oxide. Since the compositions are cast as a film, it is clear that the polymer will have a major effect on the properties of the film and on the properties of the solution before drying.

Polyacrylic acid is mentioned as material that can be included in agricultural compositions in U.S. Pat. Nos. 4,267,280 and 5,147,444.

Polyacrylamide is mentioned as a possible humidifying agent in powder compositions (that are subsequently dissolved and sprayed) in U.S. Pat. No. 5,118,338.

It is also known to include high molecular weight polymers (including acrylamide polymers) in agricultural compositions that are to be sprayed so as to have a beneficial effect on the spray pattern of the composition. These materials are generally added to increase the size of the spray droplets so as to reduce drift, and have the consequence of altering and generally reducing the spray angle. Also, such a polymer in the solution may tend to act as a sticker, to promote adhesion of the active ingredient to the leaves so as to improve persistence even if it rains soon after spraying. In practice, the materials that have generally been proposed are reverse phase emulsions, and a typical disclosure is in Canadian patents 785,706 and 1,023,264. These show, inter alia, the use of polymers formed from a significant amount of ionic monomer, with acrylamide being optional. Reverse phase materials have been commercially available under the named "Nalcotrol" from Nalco Chemical Company and "Bandrift" from Allied Colloids Limited. As described at page 20 line 5 of Canadian 1,023,264, the normal way of preparing the sprayable composition would be first to dilute or disperse the active ingredient into water to form a sprayable composition and subsequently to add the reverse phase polymer to the sprayable composition.

Despite the proposals in the literature, and the commercial availability of suitable materials, in fact there has been very little use of products such as Nalcotrol and Bandrift. The reason for this is that it seems that users considered there was insufficient economic or environmental justification for their use. For instance such materials were designed to reduce drift caused by wind, and it is contrary to good farming practice to spray when there is any wind. Also, the larger drop size that is a necessary consequence of reducing spray drift might be expected to reduce coverage and therefore to reduce activity at economic dosages.

Also, it appears that there has been some concern that the polymer might interfere with the systemic activity of the active ingredient. Thus in J Environ Sci Health, volume B25(3), 1990, pages 309 to 332 (published after the priority date of this application) Sundaram reported investigations into the effect of Nalcotrol on bio-availability of glyphosate in laboratory trials on seedlings of Trembling Aspen (Populus Tremuloids). He conducted studies into small differences in the sub-lethal effects of such compositions and concluded that there were no significant differences in the absorption and translocation patterns and growth parameters between plants treated with glyphosate alone and plants treated with glyphosate combined with Nalcotrol.

The art therefore has been concerned that polymers which are convenient lot formulation purposes, for instance for modifying the spray pattern or for inhibiting crystallisation, may have an undesirable effect on systemic performance.

OBJECTS OF THE INVENTION

One object of the invention is to provide improved systemic effectiveness of systemic active ingredient in sprayable compositions. Another object is to provide an additive for the dilution water by which the sprayable composition is made, or for the sprayable composition itself, by which improved systemic activity can be obtained in the sprayable composition. Another object is to provide a concentrate of a composition which, upon dilution with water, can be sprayed so as to provide improved systemic activity in the sprayed composition. Another object is to be able to achieve improved systemic activity without affecting the spray pattern of the composition when this is desired, since this would allow the improved activity to be obtained under spraying conditions that are not influenced by the presence of polymer.

SUMMARY OF THE INVENTION

In the invention, a sprayable aqueous composition containing a systemic, foliar, active ingredient is sprayed on to plants, and the systemic activity of the composition is improved by including an acrylamide polymer in the sprayable composition. The polymer is included in an amount which results in improved systemic activity, and which is generally from 0.005 to 0.5% by weight of the solution.

The invention also includes a sprayable aqueous composition containing a systemic, foliar active ingredient and an acrylamide polymer in an amount which results in improved systemic activity and which is generally from 0.005 to 0.5% by weight.

The invention also includes an agricultural concentrate which can be diluted with water to form a sprayable aqueous composition, wherein the concentrate contains a systemic, foliar, active ingredient and an acrylamide polymer in an amount which, when the concentrate is diluted to form a sprayable aqueous composition, results in improved systemic activity when that composition is sprayed on to plants.

The invention also includes an agricultural composition which is a concentrate which can be diluted with water to form a sprayable composition or which is a sprayable composition and which contains a systemic foliar active ingredient and an acrylamide polymer, and directions for utilising the acrylamide polymer to improve systemic activity of the composition.

The invention also includes compositions for mixing with a systemic active ingredient (for instance by inclusion in dilution water in which a concentrate of the active ingredient is diluted to make a sprayable composition, or by inclusion in a sprayable composition containing active ingredient) and directions for utilising the acrylamide polymer for improving systemic activity of the active ingredient.

For instance the composition may be in a container such as a tank, can, bottle, jar or other container and the label on the container, or written instructions with the container provided by the manufacturer (or both) may indicate the improved systemic activity obtainable by the use of the acrylamide polymer. It may include instructions relating to concentrations of the polymer in the final composition, or proportions of the polymer to the active ingredient, whereby improved systemic activity would be obtained. The instructions for utilising the acrylamide polymer may, additionally or alternatively, consist merely of an announcement in the general terms that the composition contains a component (i.e., the polymer) which will have a beneficial effect on the systemic activity of the active ingredient.

The instructions associated with the package may, additionally or alternatively, consist of or include information supplied to the regulatory authorities who licence the products for use in agriculture, such information consisting of or including information about the enhanced systemic effect that arises as a result of the inclusion of the polymer.

DESCRIPTION OF THE PREFERRED EMBODIMENTS

The invention results in the provision of acceleration of transport and translocation of the active ingredient and an improved systemic effect, and in particular an improved lethal herbicidal effect when the active ingredient is a herbicide. Thus a lethal effect is achieved at a lower dose and/or under conditions such that it would not reliably be achieved in the absence of the polymer.

In order to achieve the effect, it is essential that the polymer should be fully activated, i.e., dissolved, in the sprayable composition before spraying of that composition. The polymer can initially be provided in any convenient commercial form, for instance a powder, a reverse phase emulsion (including anhydrous reverse phase dispersions) or aqueous solutions.

The present invention is based on the surprising discovery that, when one studies a range of plants, there is an overall improvement in systemic activity when the spray droplets that contact the leaves contain a solution of certain polymers in addition to a solution or emulsion of the systemic active ingredient. Thus we have discovered that there is a significant performance benefit in the incorporation of polymers that do not substantially alter the spray pattern of the composition. Thus in the invention the molecular weight and amount of the polymer is generally such that the spray pattern of the composition is substantially unchanged (compared to the corresponding sprayable composition in the absence of polymer) but significant improvement in systemic performance is obtained.

In particular, by incorporating the polymer solution into the sprayed droplets on the leaves it is possible with many substrates to obtain the same systemic activity in the presence of the polymer as is obtained at a much higher concentration of active ingredient in the absence of the polymer. For instance it may be possible on some substrates to halve the concentration of systemic herbicide and yet still obtain a systemic lethal effect on the substrate.

It seems that the presence of the dissolved polymer results in accelerated transport and translocation of the active ingredient into the plants, with consequential improvement in the prospects of lethal effects on the plant. For instance there can be significant translocation within 45 minutes of spraying. It seems that the rain persistence or sticking properties of the sprayed composition is irrelevant to this effect, since the advantage is shown both when rain occurs and when it does not.

Although we do not wish to be bound by theory, it seems that there is some interaction between the cell wall and the sprayed solution of polymer and active ingredient whereby the polymer promotes the transfer of the active ingredient through the cell wall into the cell, but apparently does not promote the reverse transfer of the active ingredient out of the cell. The use of a polymer having pendant amide groups is particularly desirable because of the compatibility between the amide groups and the cell walls, and preferably therefore the polymer is an acrylamide polymer. The use of materials such as ammonium sulphate and urea to improve transport of glyphosate into cell walls is known but the inclusion of such materials tends to result in mere scorch of the leaves, and this is undesirable. By the inclusion of useful amounts of suitable polymer it is possible to achieve improved transport and/or translocation without incurring scorch or other phytotoxic effects.

It appears that the acrylamide units in the acrylamide polymer are involved in achieving best results, and a wide range of acrylamide polymers can be used. The acrylamide units can include methacrylamide but preferably they are of acrylamide $CH_2=CHCONH_2$.

The use of substantially non-ionic polyacrylamide is particularly preferred because it is effective, toxicologically acceptable, and compatible with a wide variety of active ingredients and other components (such as surfactants) that may be included in the compositions, irrespective of whether these other components are ionic or non-ionic. Also, substantially non-ionic polyacrylamide has less tendency to increase the viscosity of the composition (and thus potentially affect the spray pattern) than would an ionic polymer of the same molecular weight at the same dosage. The preferred polymers are therefore formed of 97 to 100% acrylamide and 3 to 0% sodium acrylate (by weight).

However other suitable polymers can contain up to 20%, or sometimes even up to 49% or more (e.g., 50 to 70%), by weight of monomers other than acrylamide, with the balance being acrylamide. These other monomers can be non-ionic but are generally anionic or cationic and are usually ethylenically unsaturated.

The preferred co-monomers are acrylic or allylic monomers that will copolymerise with acrylamide. Suitable cationic monomers include dialkylaminoalkyl -(meth) acrylates and -(meth) acrylamides usually as quaternary or acid addition salts. Suitable anionic monomers include ethylenically unsaturated sulphonic monomers such as 2-acrylamido methyl propane sulphonate and, preferably, carboxylic monomers such as (meth) acrylic acid (usually as water soluble salts).

Suitable polymers are anionic acrylamide polymers, preferably copolymers which have a content of sodium acrylate or other anionic groups of for instance up to 10% or even 20% or 30% or more, the balance being acrylamide.

Another class of suitable polymers are acrylamide cationic polymers, for instance formed from 60 to 99%, often 70 or 80 to 90 or 95%, by weight acrylamide with the balance being cationic monomer, such as any of the cationic monomers listed below. The cationic polymers are preferably not used in aqueous compositions that are to be stored for a prolonged period, since they may hydrolyse. Accordingly they should preferably be incorporated in non-aqueous concentrates or added to the sprayable compositions or the dilution water.

Instead of using acrylamide polymers, other water soluble polymers, for instance formed from blends of ethylenically unsaturated non-ionic and cationic or anionic monomer can be used provided they give the desired effect. Preferably the polymer has pendant amide groups. It should however be noted that some polymers will give a negative effect. For instance partially neutralised polyacrylic acid can reduce herbicidal effectiveness.

The polymer is preferably truly soluble in water, being a substantially linear polymer formed from a water soluble monomer or monomer blend. Less preferably when it is a reverse phase emulsion it can be a polymer that behaves, to the naked eye, as a soluble polymer in that it goes into a substantially stable dispersion of highly swollen polymer particles in water, and these particles stick to one another and to the leaves on drying. Technically however the particles are insoluble, and can be made by including not more than 30 or 40 ppm, and usually not more than 10 ppm, of a conventional polyethylenically unsaturated cross linking agent, or other cross linking agent, with the water soluble monomer or monomer blend that is polymerised to form the particles.

The invention includes the use, when spraying plants with a foliar systemic active ingredient composition, of a substantially dissolved acrylamide polymer in the composition for increasing the effectiveness of composition that contacts the plants and/or for accelerating transport and translocation of the active ingredient into and within the plant. This effect has never previously been observed and the use of acrylamide polymer for this purpose has never previously been recommended. In particular, the invention includes such uses where the active ingredient is glyphosate, and in particular such uses when applied to a variety of plant substrates. Sundaram (see above) failed to observe the effect, probably because of a combination of factors, namely he was determining the sub-lethal effect of the composition whereas the invention aims at a lethal effect (when using a herbicide), his dosages and particular techniques were therefore inadequate to give lethal effects, and he conducted tests on a single plant species. Additionally, the presence of the Nalcotrol probably had an adverse effect on the distribution of the active ingredient on the leaves for two reasons. The increased viscosity due to the Nalcotrol would probably have caused a significant increase in the particle size of the sprayed water droplets. Further, the Nalcotrol probably would not have been fully activated and thus would not have been in true solution and the amount of polymer in true solution would probably then have been inadequate to achieve improved systemic activity.

For example, the compositions of glyphosate and Nalcotrol described after the priority date in the said paper by Sundaram would have been made, by conventional techniques, by dissolving glyphosate in water and then adding Nalcotrol and then spraying. However the glyphosate is an aqueous electrolyte and so this would tend to inhibit the activation of the polymer particles which, according to Sundaram (page 311) provide a cross linked polymer chain of an unspecified polyvinyl polymer.

One aspect of the invention relates to a sprayable foliar, systemic composition that comprises a solution or dispersion of a systemic active ingredient in a continuous aqueous phase that is a substantial solution of a substantially water soluble polymer that has been introduced into the aqueous phase as a reverse phase dispersion of the polymer in an inert oil.

In this aspect of the invention, the composition preferably has been made by mixing the reverse phase polymeric composition with the aqueous phase in the absence of the active ingredient, preferably achieving substantially full activation (or dissolution) of the polymer, and thereafter mixing the active ingredient into the aqueous phase containing fully dissolved or activated polymer. This technique allows optimum activation of the polymer, and this can be manifested by the particles of the inert oil being very small. This is significant because a very small and relatively uniformparticle size indicates that there has been very thorough distribution of the reverse phase polymeric composition into the aqueous phase of the sprayable composition and this very thorough distribution will inevitably have promoted substantially full activation and dissolution of the polymer.

In the described compositions, the oil is preferably present in the aqueous phase as an emulsion of oil particles having a weight average particle size of below 25 μm. As indicated above, such a composition can best be made by distributing the reverse phase polymer in the water before adding the active ingredient. However such compositions are not limited to having been made by the above order of addition since careful choice of emulsifiers and mixing conditions and active ingredient will permit this unique particle size (and good activation of the polymer) to be obtained even when the reverse phase composition is added to a previously formed solution or emulsion of the active ingredient.

Preferably the particle size of the inert oil particles is below 20 μm and most preferably it is below 10 μm. Preferably the particle size distribution is relatively narrow. Preferably the number average particle size is within 30%, and preferably within 15%, of the weight average particle size. For instance when the mean particle size (ie weight average) is in the range 10 to 20 μm, the median particle size (i.e., number average) may be from 1 to 2, or at the most 3, μm smaller or larger than the mean particle size.

In order to promote the formation of these very small oil particles, and thus full activation of the polymer, it is desirable to increase the self-emulsifying properties of the reverse phase dispersion in water, as well as being desirable to emulsify this composition in water before adding the active ingredient. For instance conventional addition of materials such as Bandrift or Nalcotrol typically will give an oil particle size in the range 50 to 100 μm or more but in the invention a much smaller particle size is obtained by an appropriate combination of mixing conditions and oil-in-water emulsifier. For instance if the composition contains a significantly more effective oil-in-water emulsifying system than conventional, the desired particle size may be obtained merely by pouring the composition into water without any particular agitation.

The small particles of oil seem to give an additional benefit over and above the benefit that is derived from the fact that they are associated with the polymer being well activated. This benefit arises because the oil particles will cover a much larger surface area of the leaf than will be covered by the conventional larger oil particles. For instance if the oil particle diameter is half the conventional diameter then this will give an eight-fold increase in the number of droplets and if the diameter is one third then it will give a twenty seven-fold increase in the number of droplets. This increase in the number probably increases the surface area that is covered by surface coverage by oil droplets and this may promote penetration of the wax cuticle layer.

The invention also includes a method of systemic control of plants by spraying plants with an aqueous composition that is a solution or dispersion of a systemic active ingredient in a continuous aqueous phase, that is a substantial solution of a substantial water soluble polymer, that has preferably been introduced into the aqueous phase as a reverse phase dispersion in the general manner described above. Often the active ingredient is a herbicide and the method involves killing of the plants. Preferably the area that is sprayed contains a plurality of varieties of plants, most or all of which preferably are killed by the treatment. In other instances there is one persistent weed in an otherwise empty crop area (e.g., couch grass) or there are a plurality of weeds amongst resistant plants such as relatively mature trees.

The reverse phase polymers used in the invention can have a wide range of molecular weights. However in the invention the polymers are normally polymers that have a viscosity such that they affect the spray drift and spray droplet properties as a result of their viscosity and so will have a relatively high molecular weight, which in practice means intrinsic viscosity generally above 3 dl/g, often above 4 dl/g, for instance 7 to 15 dl/g. However higher intrinsic viscosities can be used.

When the polymer is added as a reverse phase dispersion the weight ratio of polymer to oil is often in the range 1:0.7 to 1:4, often around 1:1.5 to 1:3, and the amount of oil-in-water emulsifying agent is often in the range 2 to 5% based on oil and polymer.

The size of the polymer particles in the reverse phase emulsion should be at least 90% below 3 μm and the formation of the small particles is promoted by including in the reverse phase polymerisation mixture a conventional water-in-oil emulsifying agent (typically having HLB 3-7), such as sorbitan mono-oleate, typically in an amount of 1–5%. Stability of the dispersion during and after polymerisation is frequently improved by including 1–5% of an amphipathic polymeric stabiliser such as a 2:1 copolymer of cetostearyl methacrylate:methacrylic acid.

Reverse phase polymerisation can be initiated and conducted in conventional manner to produce a reverse phase emulsion of aqueous polymer particles dispersed in inert oil.

The amount of water in the dispersion is typically from 1:2 to 1:0.5 parts per part polymer. The emulsion can be used as such but preferably it is dehydrated by azeotropic distillation until it is substantially dry, in known manner.

Oil-in-water emulsifier, typically having HLB above 7, must be present in order to promote distribution of the reverse phase emulsion into water, and to promote activation of the polymer. This can be included in the reverse phase emulsion or can be added separately. If the polymer is added in a form whereby it is not already mixed with appropriate emulsifiers for promoting the distribution of polymer and/or active ingredient into the sprayable composition and/or for wetting the leaves, then such emulsifiers can be added separately, in known manner.

The inert oil of the reverse phase emulsion can be any of the water immiscible, non-aqueous, solvents that can conveniently be used as the continuous phase of a reverse phase polymer emulsion.

The systemic active ingredient that is included can be a plant growth promoter (such as a nutrient), a plant growth regulator, or a pesticide, for instance an insecticide or fungicide or, preferably, a herbicide. Preferably it is soluble in water, most preferably being glyphosate (generally as a water soluble salt) or a potassium, sodium or amine or other water soluble salt of hormone herbicides such as 2,4-D, or CMPP or MCPA.

Water insoluble active ingredients that can be used include Bromoxynil, Ioxynil and Pentanochlor. A water insoluble active ingredient can sometimes conveniently be introduced as a solution in the oil phase of a reverse phase dispersion of polymer. It can then be convenient to incorporate the active ingredient as a solution in oil that is miscible with the inert oil of the reverse phase dispersion.

If the active ingredient is being supplied separately, it can be supplied in any of the conventional forms such as aqueous solutions, water soluble powders or granules, emulsifiable concentrates, oil-in-water emulsions, and so forth.

The composition can be supplied by providing a concentrate and obtaining an agricultural sprayable composition as described above can be obtained by dilution with water. The concentrate can include the foliar active ingredient, but frequently the foliar active ingredient is supplied separately.

The concentrate preferably self-emulsifies into water at 20° C., and preferably at lower temperatures such as 10° C. or even 5° C., in order that the desired small particle size is obtained easily upon the addition of the concentrate to water, without any special mixing requirements and preferably spontaneously. Preferably mixing of the type conventionally used for making up sprayable compositions is used so as to ensure uniform distribution of the concentrate throughout the dilution water.

The amount of active ingredient in the concentrate, on a dry weight basis, typically is 20 to 60% (preferably 20–40%) polymer, 35 to 75% (preferably 50–75%) oil and 3 to 15% (preferably 5–10%) oil-in-water emulsifier. The concentrate typically is added to water at a rate of about 0.01 to 1%, often 0.03 to 0.3%, typically to give a polymer concentration of 0.005 to 0.1% or even 0.5 (often 0.01 to 0.05%) and an oil concentration of 0.005 to 0.5% (often 0.03 to 0.1%). The amount of active ingredient typically is 0.1 to 5%, often 0.3 to 2%.

The amount of polymer that is incorporated is generally at least 25 grams and frequently at least 100 grams per 1,000 liters of sprayable composition. If the amount is too high it will tend to interfere unacceptably with spray patterns and so generally the amount is not more than around 250 or 300 grams in 1,000 liters.

The invention is of particular value in the herbicidal treatment of a variety of crop areas and these can include forestry; clean-up of cereal crops before harvest; autumn field clean-up; and use on waxy-headed varieties common in Mediterranean climates.

The invention also includes methods in which the described composition is sprayed on to growing plants and the active ingredient is thereby absorbed through the leaves of the plant to exert a systemic activity.

The invention also includes a process of controlling plants comprising the steps of forming a sprayable foliar systemic herbicidal composition containing glyphosate by dispersing into water a reverse phase composition comprising water soluble polymeric material dispersed in an inert oil and thereby emulsifying the inert oil into the aqueous phase and dispersing or dissolving the polymeric material into the aqueous phase, subsequently dissolving the glyphosate into the aqueous phase, and spraying the resultant solution on to growing plants and thereby killing them.

In another aspect of the invention, instead of introducing these relatively high molecular weight or viscosifying polymer from a reverse phase emulsion, it is introduced as powder. This is less convenient because it is essential to achieve full dissolution of the powder, and the agricultural user may sometimes find it inconvenient to conduct adequate mixing to achieve full dissolution. Any of the conventional methods and mixing apparatus known for achieving full dissolution of water soluble viscosifying polymers can be used. It is particularly preferred that the polymer particles should have a surface coating that promotes dissolution of the particles and minimises agglomeration of the particles during dissolution. Suitable coatings include hydrophilic siliceous materials and inorganic hydrates. Preferred coatings are described in EP-A-598,730 and in U.S. Ser. No. 07/960,397 filed 15th January 1993 by Peter Flesher, Malcolm Skinner, David Farrat and Brian Dymond, the entire disclosure of which is herein incorporated by reference.

Although the viscosifying or relatively high molecular weight polymer compositions described above do give useful improvement in systemic activity, they will normally affect the spray drift and spray droplet properties, and this can be unnecessary and even undesirable in some instances. It would therefore be desirable to be able to achieve the improvement in systemic activity without affecting the spray pattern of the composition and without the use of a high molecular weight polymer that could, with inadequate mixing or activation, cause blockage of the spray nozzles. Accordingly it would be desirable to be able to achieve the effect with low molecular weight polymers.

In particular when the active ingredient is water soluble, it would be desirable to provide a fluid, and easily dilutable, concentrate containing both the active ingredient and the polymer dissolved in water.

In another aspect of the invention, a sprayable foliar composition comprises a solution or dispersion of a systemic active ingredient in a continuous aqueous phase and is characterised in that the continuous phase is an aqueous solution of a systemically useful amount (generally 0.005% to 0.5% by weight of solution) of a water soluble polymer having a low molecular weight. Preferably the polymer and its amount are such that its presence in the composition does not substantially affect the spray pattern of the composition and/or is the polymer is such that it can be, and preferably is, supplied as an aqueous solution of 1 to 25% polymer. This necessitates that the polymer is of low molecular weight.

The invention also comprises a method in which such a composition is sprayed on to growing plants and the active ingredient is thereby absorbed from the solution through the leaves of the plants to exert a systemic activity.

The invention also comprises an aqueous concentrate that can be diluted in water to form a sprayable foliar systemic composition and that is a solution of water soluble foliar systemic active ingredient and 1 to 25%, by weight of the concentrate, of a water soluble polymer dissolved in the concentrate.

The molecular weight of the polymer is preferably quite low since this facilitates manufacture, formulation and use, and there is no advantage in the invention in increasing the molecular weight. Generally the preferred molecular weight is such that the polymer has intrinsic viscosity below 4 dl/g and generally below 3 dl/g, but preferably above 0.2 or 0.5 and most preferably above 1 dl/g, with an intrinsic viscosity of around 2 dl/g generally being preferred.

Intrinsic viscosity is measured by suspended level viscometer at 25° C. in 1N buffered sodium chloride solution.

Molecular weight (determined by gel permeation chromatography) is generally below 4 million and is frequently in the range 100,000 to 1 million, but it can be below 100,000 and as low as, for instance, 30,000 or even less, for instance down to 15,000, 10,000 or even 5,000. However it is considered unacceptable to expose monomeric acrylamide to the environment and the risk of monomeric acrylamide contamination may increase as the molecular weight decreases and this makes it desirable to avoid extremely low molecular weights.

The amount of low molecular weight polymer that is required in the spray solution to achieve improved systemic activity can be similar to the amount of high molecular weight polymer. It can be determined by routine experimentation and will depend upon the plant, the polymer and the active ingredient. It is generally in the range 0.005 to 0.5% (by weight of solution). In many instances it is desirable to include at least 0.01, and often at least 0.02% in order to obtain a useful effect, and frequently it is found that there is a significant improvement as the concentration increases up to, for instance, about 0.05% or 0.1%. However there is generally no benefit in increasing the polymer concentration above around 0.1 or, at the most, 0.2% but if desired higher amounts can be used.

Whether or not the presence of the chosen amount of the chosen low molecular weight polymer does substantially alter the spray pattern of the composition can easily be determined merely by spraying the composition, with and without the dissolved polymer in it, through a spray bar that is otherwise unchanged for both tests. Another way of determining whether the spray pattern is substantially altered is by observing the particle size of the spray droplets. Conventional spray-drift polymers and stickers will tend to result in a significant increase in average particle size of the spray droplets. By saying that the presence of the polymer does not substantially affect the spray pattern of the composition we mean that the spray pattern (or the particle size) is affected much less by the presence of the defined polymer than when conventional amounts (typically 0.02%) of a conventional spray drift polymer or sticker is added, and preferably the droplet size and the spray pattern of the composition of the invention is substantially the same as the droplet size and the spray pattern of the same composition from which the polymer has been omitted.

Although it is preferred that the low molecular weight polymer does not substantially affect the spray pattern of the composition, the invention can also include compositions in which the polymer can have some effect on the spray pattern although this is less desirable. Such compositions are preferably made by forming the compositions by diluting an aqueous solution of from 1 to 25% by weight of the polymer, either as a polymeric additive to the composition or as a concentrate containing the active ingredient and the polymer.

Thus whereas polymers traditionally used as spray drift inhibitors cannot conveniently be supplied to the user as a solution, because of the high viscosity of aqueous solutions of them, in the invention the polymer can have such a low molecular weight that it can be supplied to the user as a fluid solution of polymer in water. The polymer solution that is supplied to the user preferably has a polymer content of at least 3% and often at least 5% (these concentrations being impracticable for spray drift inhibitors). Although the amount is often below at least 10%, it can be more. Generally it is unnecessary for the amount of polymer to be too high, for instance above 25%, and generally it is convenient for the polymer concentration to be below 20% and more usually below 15%.

When the active ingredient is water soluble, it is generally supplied as an aqueous concentrate, i.e., a solution of the active ingredient in water. The amount of active ingredient will be selected according to its solubility, but is often above 10% and frequently above 30%, and can be as high as 60% or even 75% by weight of the concentrate.

It is particularly preferred to provide an aqueous concentrate that is a solution of Chlormequat or other water soluble active ingredient and low molecular weight polyacrylamide or other polymer.

The amount of active ingredient can be conventional for that active ingredient. The amount of polymer is generally at least 1%, often at least 3% and frequently at least 5%. Usually it is not more than 10% but it can be more, for instance up to 15, 20 or even 25% by weight.

The amount of polymer can, of course, be less than 1% if the concentrate is more dilute than conventional agricultural concentrates.

Instead of supplying the active ingredient as an aqueous solution, it can be supplied in any of the other conventional forms such as oil-in-water emulsions, suspension concentrates, emulsifiable concentrates, and water dispersible grains. The choice of the type of composition will depend on the solubility of the active ingredient.

Preferred water soluble active ingredients are Glyphosate, Chlormequat, Diquat, Clopyralid and hormone—weedkillers, such as Mecoprop, 2,4-D, CMPP or MCPA, for instance supplied as a potassium, sodium or amine or other water soluble salt.

Water insoluble active ingredients that can be used include Bromoxynil, Ioxynil, Pentanochlor, Sethoxydim and Fluazifop-p-Butyl. Others, and the form in which they are conveniently supplied, include Fenoxaprop-ethyl (oil-in-water emulsion), Quizalofop-ethyl (suspension concentrate), Fluroxypyr (emulsifiable concentrate), Metsulfuron-methyl (water-dispersible grain), and Isoproturon (suspension concentrate).

These active ingredients are of use in all aspects of the invention. The active ingredient is preferably a plant growth regulator (for instance Chlormequat which can be used as a plant growth regular in cereals) or the active ingredient can be used as a herbicide.

The invention is of particular value in the herbicidal treatment of a variety of crop areas and these can include forestry; clean-up of cereal crops before harvest; autumn field clean-up; and use on waxy-headed varieties common in Mediterranean climates. In such methods the active ingredient is a herbicide and the method involves killing of the plants. Preferably the area that is sprayed contains a plurality of varieties of plants, most or all of which preferably are killed by the treatment. In other instances there is one persistent weed in an otherwise empty crop area (e.g., couch grass) or there are a plurality of weeds amongst resistant plants such as relatively mature trees.

The amount of active ingredient in the sprayable composition that is to be sprayed on to the fields or plants may be selected according to normal recommended instructions. These instructions may be provided with or on the container which contains the active ingredient, and optionally also the polymer. The concentration is typically in the range 0.1 to 5%, often 0.3 to 2%, by weight of the sprayable composition. The rate of application of the active ingredient to the plants can be less than the amount that would normally be recommended as optimum. For instance by the invention it is possible to obtain good results even though the amount of active ingredient that is sprayed on to the fields is in the range 50 to 80% or 90% of the amount that would normally be recommended. However the invention can also be utilised by spraying the active ingredient at a dosage which is conventional but under conditions that would normally be considered adverse to effective results. For instance it is normally recommended that the active ingredient should be applied during warm growing conditions but the extra effectiveness achievable in the invention can result in good results being achieved when the dosage that would normally be used for warm application is used when the ambient growing conditions are poor, for instance due to low temperatures.

An important result of the invention is that the presence of the polymer results in the active ingredient generally having a better spectrum of activity on a range of plants or pests but it does not guarantee that it will have better activity on every individual plant variety or pest. Accordingly, although there may be an overall improvement in the spectrum of activity against various plants, there may be a few isolated instances where activity is worse with the polymer than without. However this does not detract from the fact that the presence of polymer clearly gives a benefit in the overall spectrum of activity, against other plants, with the result that the invention gives the opportunity for frequently reducing the dosage of active ingredient that is required in general field use. Accordingly, although some of the examples show isolated instances where activity against a particular plant at a particular dosage is worse with the polymer than without, in practice the polymer increases the spectrum of activity against various plants and so in practice the polymer gives beneficial results against a range of plants even though it may not show an improvement in one particular test against one particular plant.

The following are some examples of the invention.

EXAMPLE 1

Three dehydrated reverse phase emulsions A, B and C of non-ionic polyacrylamide were made by reverse phase emulsion polymerisation in conventional manner to a polymer particle size of below 3 μm and IV in the range 5 to 8 dl/g. Dispersion A is typical of commercial agricultural sticker compositions. Dispersions B and C are dispersion suitable for the invention but the increased amount of oil in Dispersion B results in it being preferred. The emulsions (dispersions) have the following analysis. The emulsion particle size is below about 3 μm.

|   | Dispersion A | Dispersion B | Dispersion C |
| --- | --- | --- | --- |
| 1. Non-ionic polyacrylamide | 50 | 25 | 50 |
| 2. W/O emulsifier HLB 4.3 | 1.0 | 1.17 | 2.79 |
| 3. Amphipathic stabiliser | 1.7 | 1.76 | 2.35 |
| 4. O/W emulsifier | 4.0 | 6.59 | 5.66 |
| 5. Hydrocarbon oil | 43.3 | 64.8 | 37.8 |

Component 1 has molecular weight about 5 million

Component 2 is sorbitan mono-oleate

Component 3 is 2:1 copolymer of cetostearyl methacrylate and methacrylic acid

Component 4 is a blend of 2 parts nonyl phenol ethoxylate (5 moles ethylene oxide HLB 10.5) with 1 part $C_{12-15}$ alcohol ethoxylate (4 moles ethylene oxide, HLB 9.8)

Component 5 is Pale Oil 150

Sprayable solutions were prepared by gently mixing intro 1 liter water 16 ml of a 480 g/l aqueous solution Glyphosate (as amine salt) and 0.5 ml of Dispersions A or C or 1 ml Dispersion B.

The compositions were made either by a "pre-addition" technique (in which the polymer dispersion was dissolved in the water before adding the glyphosate) or by a "post-addition" technique in which the glyphosate was dissolved before adding the polymer.

The median and mean oil particle sizes (μm) were recorded for "post-addition" and "pre-addition".

|  | Pre-addition | | Post-addition | |
| --- | --- | --- | --- | --- |
|  | median | mean | median | mean |
| Dispersion A | 27 | 36 | about 100 | about 100 |
| Dispersion B | about 1 | about 1 | 20 | 32 |
| Dispersion C | 10 | 7 | 12 | 17 |

When sprayed on to vegetation, compositions A are least effective and composition B made by pre-addition is the most effective.

EXAMPLE 2

Winter barley (variety Igri) was grown in trays of compost (10 seeds per tray) in a growing room.

At the 2 leaf stage, the barley plants were sprayed with their respective treatment.

Each treatment was replicated 3 times. Treatments were applied using a propane pressurised sprayer, fitted with a rotary belt on which the trays were placed. A volume of water equivalent to 500 liter/hectare (5 l/km$^2$) was used at a pressure of 3.0 bar ($3 \times 10^5$ Pa), through a Lurmark 015 F80 flat fan nozzle.

Glyphosate was sprayed at two concentrates, at doses known to be sub-lethal, with and without Adjuvant D, which is a dehydrated reverse phase emulsion containing:

| 1. Non-ionic polyacrylamide (IV = 8 dl/g) | 25.0% |
| --- | --- |
| 2. Water-in-oil Emulsifier HLB 4.3 | 1.1% |
| 3. Amphipathic stabiliser | 1.7% |
| 4. Oil-in-water Emulsifier | 7.0% |
| 5. Hydrocarbon oil (Pale Oil 150) | 65.2% |
|  | 100.0% |

Component 2 is a sorbitan mono-oleate

Component 3 is a 2:1 copolymer of cetostearyl methacrylate and methacrylic acid.

Component 4 is a blend of 2 parts nonylphenol ethoxylate (5 mole ethylene oxide HLB 10.5) with 1 part $C_{12-15}$ alcohol ethoxylate (4 mole ethylene oxide, HLB 9.8)

This product was added directly to the spray tank at a rate of 0. 1% of the spray volume (equivalent to a polymer dosage of 0.025%), prior to addition of glyphosate.

Some trays were subjected to "rainfall"; this consisted of treating the trays with 5mm of water from the spray, 45 minutes after initial treatment. The results are summarised in Table 1 in which the percentage regrowth is an indication of the extent of growth obtained after the specified time (day 3 or day 13) after cutting the plant down subsequent to spraying. The percentage kill is a subjective assessment taken at day 17 as to the percentage of plants that have died or are dying.

TABLE 1

| Treatment No. | 1 | 2 | 3 | 4 | 5 | 6 | 7 |
| --- | --- | --- | --- | --- | --- | --- | --- |
| Glyphosate (grams/ha) | 0 | 250 | 250 | 375 | 375 | 375 | 375 |
| Adjuvant | 0 | 0 | +D | 0 | 0 | +D | +D |

TABLE 1-continued

| Treatment No. | 1 | 2 | 3 | 4 | 5 | 6 | 7 |
|---|---|---|---|---|---|---|---|
| Rainfall | − | − | − | − | + | − | + |
| Regrowth % | | | | | | | |
| Day 3 | 100 | 22.4 | 21.4 | 8.8 | 21.0 | 7.0 | 16.0 |
| Day 13 | 100 | 30.2 | 21.7 | 19.0 | 19.1 | 4.7 | 10.7 |
| Kill % | 0 | 28 | 55 | 70 | 48 | 80 | 55 |

It can be seen that both dose levels of glyphosate, the presence of Adjuvant D enhances the activity of glyphosate, as shown by the reduction in regrowth, and the increase in kill.

In presence of rain, the activity of glyphosate is reduced, but the presence of Adjuvant D still leads to increased efficacy of glyphosate.

EXAMPLE 3

Glyphosate was sprayed at a dosage of 250 g/ha, in a spray volume of 150 l/ha. Adjuvant D, where included, was present at a rate of 0.1% of the spray volume (150 ml/ha), by addition to the water before the glyphosate is dissolved in it.

The plot was sprayed during an overcast dry spell with a temperature of 17° C. The foliage was damp, the relative humidity was 80% and no rain fell during the next 2 hours.

Reduction in Green Plant Mass (%) was assessed approximately one month later and the results are in Table 2.

TABLE 2

| | Glyphosate I | | Glyphosate II | | Glyphosate III | |
|---|---|---|---|---|---|---|
| | −D | +D | −D | +D | −D | +D |
| Birch | 70 | 100 | 90 | 100 | 70 | 95 |
| Hazel | 30 | 50 | 42 | 20 | 10 | 10 |
| Rowan | 70 | 100 | 70 | 90 | 50 | 70 |
| Raspberry | 20 | 20 | — | — | 10 | 10 |

The trial site had spruce trees of approximately 10 years maturity on it and there was no damage to these by the spraying with any of the formulations.

EXAMPLE 4

Dosages and spray volumes were identical to those in Example 3.

The plot was sprayed during a hazy dry spell. The temperature was 18° C. with relatively high humidity.

Reduction in Green Plant Mass (%) was assessed approximately one month later. The results are summarised in Table 3.

TABLE 3

| | Glyphosate I | | Glyphosate II | | Glyphosate III | |
|---|---|---|---|---|---|---|
| | −D | +D | −D | +D | −D | +D |
| Birch | 20 | 60 | 30 | 60 | | |
| Hazel | 20 | 80 | 10 | 60 | 25 | 20 |
| Aspen | — | — | | | 20 | 20 |
| Black Alder | 10 | 40 | 10 | 10 | | |

Field results involving the use of glyphosate are always subject to the types of variations obtained in examples 2 and 3. However, it is evident that for most trials run, in either example, that the presence of adjuvant D in the formulation increases the efficacy of the glyphosate.

In each of these examples the amount of active ingredient is calculated on the amount equivalent to glyphosate, but in practice the active ingredient was generally introduced as the isopropylamine salt of glyphosate (with 480 grams of the salt being equivalent to 360 grams of the glyphosate).

EXAMPLE 5

An aqueous solution of the polymer was formed by mixing adjuvant D with water and glyphosate was then added. In other tests glyphosate was added to water in the absence of D. the solution was then used in field trials and the percentage kill was recorded. The results are shown in Table 4.

TABLE 4

| | Percentage Kill | | | | |
|---|---|---|---|---|---|
| Glyphosate (L/ha) | 0 | 1 | 1 | 2 | 2 |
| Adjuvant | 0 | 0 | +D | 0 | +D |
| Couch Trial | | | | | |
| 1 | 0 | 82.5 | 89.5 | 89.5 | 93.8 |
| 2 | 0 | 73.8 | 80.0 | 85.8 | 90.8 |
| 3 | 0 | 67.5 | 68.8 | 73.8 | 78.8 |
| 4 | 0 | 81.8 | 89.5 | 89.0 | 94.5 |
| Annual Meadowgrass Trial | | | | | |
| 5 | 0 | 85.8 | 90.0 | 90.0 | 94.5 |
| 6 | 0 | 83.8 | 90.0 | 90.8 | 92.3 |
| Sowthistle | | | | | |
| Trial 5 | 0 | 32.5 | 47.5 | 47.5 | 56.3 |

This shows that the lower concentration of glyphosate with polymer is frequently as effective as the higher concentration without polymer.

EXAMPLE 6

Non-ionic polyacrylamide having intrinsic viscosity 2 dl/g was supplied as a 12.5% solution in water, A sprayable composition containing glyphosate was prepared in conventional manner and was either used as such (at 250 or 375 grams active ingredient per hectare) or was used after adding the polymer solution to the glyphosate solution at a dosage of 0.025% polymer, The resultant solutions were sprayed on to winter barley (variety Igri) at the 2 leaf growth stage in trays of compost in a growing room, The leaves of the sprayed plant were subsequently cut down just above the growing point to remove any non-translocated glyphosate and after 16 days an assessment was made as to the number of plants that had died or were dying, When the glyphosate was sprayed at 250 grams the estimate of kill was 20% without polymer and 50% with polymer. When the glyphosate was sprayed at the rate of 375 grams, the estimate of kill was 40% without the polymer and 85% with the polymer.

EXAMPLE 7

The process of Example 6 was repeated at different dosages of glyphosate isopropylamine salt per hectare in 250 liters water with and without 0.1% of the polyacrylamide in the spray solution. Five days after application, the plants were cut off just above the growing point and six days later the regrowth was cut and weighed and an assessment made of the number of dead plants. The results are in Table 5.

TABLE 5

| Glyphosate (g/ha) | 0 | 120 | | 240 | | 360 | |
|---|---|---|---|---|---|---|---|
| Polymer (%) | 0 | 0 | 0.1 | 0 | 0.1 | 0 | 0.1 |
| Regrowth (%) | 100 | 100 | 81.6 | 86.8 | 27.8 | 8.1 | 3.4 |
| Kill (%) | 0 | 0 | 18.4 | 13.2 | 72.2 | 91.9 | 96.6 |

EXAMPLE 8

The process of Examples 7 was repeated in a different series of trials except that different amounts of the polymer were used and the assessment was made after 15 days. The results are shown in Table 6.

TABLE 6

| Glyphosate (g/ha) | 0 (Control) | 375 | 375 | 375 | 375 |
|---|---|---|---|---|---|
| Polymer (%) | 0 | 0 | 0.025 | 0.05 | 0.1 |
| Regrowth (%) | 100 | 62.1 | 56.7 | 43.0 | 30.2 |
| Kill (%) | 0 | 40 | 40 | 50 | 70 |

EXAMPLE 9

The process of Example 7 was repeated with non-ionic polyacrylamide as in Example 7, with anionic polyacrylamide IV 2.7 dl/g formed from 72% acrylamide and 28% sodium acrylate, and with cationic polyacrylamide having IV 3 dl/g and formed from 90% acrylamide and 10% trimethyl ammonium ethyl acrylate. The results are shown in Table 7.

TABLE 7

| Glyphosate (g/ha) | 0 | 375 | 375 | 375 | 375 |
|---|---|---|---|---|---|
| Polymer | 0 | 0 | Neutral | Anionic | Cationic |
| Regrowth % | 100 | 20.6 | 13.7 | 11.9 | 6.4 |
| Kill % | 0 | 79.4 | 86.3 | 88.0 | 93.6 |

Tables 5 to 7 show the improved performance of glyphosate in the presence of low molecular weight acrylamide polymer.

EXAMPLE 10

The process of Example 7 was repeated in a different series of tests in which assessment was made after 13 days. In one test the same polymer was used as in Example 7. In another test a polymer was used which had similar molecular weight but was polyacrylic acid partially neutralised to pH 5.5.

The results are shown in Table 8 from which it is apparent that this polymer that is not made from acrylamide worsens the herbicidal effect.

TABLE 8

| Glyphosate (g/ha) | 0 | 375 | 375 | 375 |
|---|---|---|---|---|
| Polymer | — | — | Poly-acrylamide | Polyacrylic acid |
| Regrowth (%) | 100 | 25.7 | 19.0 | 66.2 |
| Kill (%) | 0 | 74.3 | 81.0 | 33.8 |

EXAMPLE 11

A concentrate of 70% Chlormequat chloride was diluted with water and sprayed at 250 l/ha to give 1208 and 1610 g/ha of Chlormequat chloride, with and without 0.1% polymer in the solution. The solutions were sprayed in a replicated field trial on to winter wheat variety Beaver (known to give good response to Chlormequat) at growth stage 31 following standard agricultural practice and immediately prior to harvest samples of wheat were taken from test pilots and the straw length measured. The same process was also applied to winter wheat variety Riband (known to give poor response to Chlormequat) and to winter barley variety Marinka. The results are shown in Table 9.

TABLE 9

| Chlormequat g/ha | 0 | 1208 | | 1610 | |
|---|---|---|---|---|---|
| Polymer % | 0 | 0 | 0.1 | 0 | 0.1 |
| Straw Length (cm) | | | | | |
| Beaker | 85.3 | 73.3 | 69.6 | 71.6 | 70.7 |
| Riband | 80.3 | 76.4 | 75.8 | 76.6 | 75.7 |
| Mariuka | 103.1 | 94.3 | 90.0 | 96.3 | 91.1 |

EXAMPLE 12

34 parts of a 12.5% aqueous solution of substantially non-ionic polyacrylamide having IV 2 dl/g was mixed with 66 parts of a 70% by weight aqueous solution of Chlormequat chloride to give an aqueous concentrate containing 46% Chlormequat chloride and 4.3% polymer. This solution was physically and chemically stable.

EXAMPLE 13

The concentrate of Example 12 was diluted in 250 l water to produce a sprayable composition that was sprayed at 1070 and 1610 g/ha Chlormequat in a replicated field trial on to winter barley variety Magi at growth stage 30 (as in Example 11) and it was also sprayed at 1610 g/ha on to linseed, with the straw length or crop height being recorded just prior to harvest. The results are shown in Table 10.

TABLE 10

| Chlormequat g/ha | 0 | 1070 | | 1610 | |
|---|---|---|---|---|---|
| Polymer | 0 | 0 | Ex 5 | 0 | Ex 5 |
| Wheat Straw Length (cm) | 102.2 | 98.9 | 97.6 | 100.8 | 95.8 |
| Linseed height (cm) | 54 | | | 53.7 | 50.4 |

The benefit of providing the Chlormequat with polymer as in Example 12, compared to the application of Chlormequat alone, is clearly shown.

EXAMPLE 14

A commercial formulation of the herbicide and potato dessicant Diquat was diluted to give a sprayable solution containing 400 g/ha, with and without 0.1% non-ionic polyacrylamide intrinsic viscosity 2 dl/g. The solution was sprayed in a replicated field trial on to Pentland Dell potato crop three weeks prior to harvest and the level of dessication was assessed at various times after spraying on a scale 0 to 9 where 0 represents the crop being completely dead and 9 represents the crop showing no damage or reduction in growth. The results are shown in Table 11.

TABLE 11

| Days after spraying | 7 | 14 | 21 |
|---|---|---|---|
| (Control) | 8.0 | 6.0 | 5.0 |
| Diquat | 7.3 | 4.3 | 1.7 |
| Diquat + 0.1% Polymer | 5.7 | 1.5 | 1.0 |

EXAMPLE 15

The same polymer as in Example 6 was used in a series of tests, the results of which are set out in Tables 12 to 19. In each instance the defined active ingredient was diluted to give the quoted dosage in g/ha with or without the poller in the specified amount and the level of kill assessed on a scale of 0 to 9, as above. In Table 12 the spray was applied on to pots of *T. maritimum* (May weed) at the 2 to 4 leaf stage. In Table 13 it was applied on to *A. myosuroives* (black grass). In Table 14 it was applied on to *A. fatua* (wild oats). In Table 15 it was applied on to *G. aparine* (cleaver). In Table 16 it was applied on to *E. repens* (common couch). In Table 17 it was applied on to *S. media* (chickweed). In Table 18 it was applied on to *V. arvensis* (field pansy). In Table 19 it was applied on to *V. persica* (speedwell).

TABLE 12

| Days after spraying | 7 | 14 | 21 | 28 |
|---|---|---|---|---|
| Control | 9.0 | 9.0 | 9.0 | 9.0 |
| Clopyralid (50 g) | 5.2 | 4.0 | 4.0 | 3.0 |
| Clopyralid (50 g) + 0.025% + Polymer | 5.0 | 4.0 q | 2.3 | 1.5 |
| Clopyralid (25 g) | 5.0 | 4.0 | 4.5 | 3.8 |
| Clopyralid (25 g) + 0.025% + Polymer | 5.0 | 4.0 | 2.8 | 1.8 |

TABLE 13

| Days after spraying | 7 | 14 | 21 | 28 |
|---|---|---|---|---|
| Control | 9.0 | 9.0 | 9.0 | 9.0 |
| Fenoxaprop-ethyl (120 g) | 6.8 | 5.8 | 4.5 | 2.8 |
| Fenoxaprop-ethyl (120 g) + 0.1% Polymer | 6.3 | 5.0 | 3.5 | 2.0 |
| Fenoxaprop-ethyl (60 g) | 7.3 | 5.8 | 4.3 | 3.3 |
| Fenoxaprop-ethyl (60 g) + 0.1% Polymer | 7.0 | 5.7 | 3.8 | 2.8 |

TABLE 14

| Days after spraying | 7 | 14 | 21 | 28 |
|---|---|---|---|---|
| Control | 9.0 | 9.0 | 9.0 | 9.0 |
| Fenoxaprop-ethyl (120 g) | 5.7 | 5.7 | 3.7 | 1.3 |
| Fenoxaprop-ethyl (120 g) + 0.1% Polymer | 5.2 | 5.5 | 3.2 | 1.3 |

TABLE 14-continued

| Days after spraying | 7 | 14 | 21 | 28 |
|---|---|---|---|---|
| Fenoxaprop-ethyl (60 g) | 6.2 | 6.0 | 4.7 | 3.2 |
| Fenoxaprop-ethyl (60 g) + 0.1% Polymer | 5.3 | 5.3 | 3.5 | 1.8 |

TABLE 15

| Days after spraying | 7 | 14 | 21 | 28 |
|---|---|---|---|---|
| Control | 9.0 | 9.0 | 9.0 | 9.0 |
| Mecoprop-P (600 g) | 6.0 | 3.5 | 3.7 | 2.0 |
| Mecoprop-P (600 g) + 0.1% Polymer | 6.0 | 3.3 | 2.2 | 0.8 |
| Mecoprop-P (300 g) | 6.0 | 3.5 | 3.5 | 2.0 |
| Mecoprop-P (300 g) + 0.1% Polymer | 6.0 | 3.3 | 2.2 | 1.2 |

TABLE 16

| Days after spraying | 7 | 14 | 21 | 28 |
|---|---|---|---|---|
| Control | 9.0 | 9.0 | 9.0 | 9.0 |
| Quizalofop-ethyl (125 g) | 8.0 | 4.8 | 3.8 | 2.3 |
| Quizalofop-ethyl (125 g) + 0.1% Polymer | 7.3 | 4.2 | 2.5 | 0.7 |
| Quizalofop-ethyl (62.5 g) | 8.0 | 4.8 | 3.7 | 0.8 |
| Quizalofop-ethyl (62.5 g) + 0.1% Polymer | 7.7 | 3.8 | 1.8 | 0.0 |

TABLE 17

| Days after spraying | 7 | 14 | 21 | 28 |
|---|---|---|---|---|
| Control | 9.0 | 9.0 | 9.0 | 9.0 |
| Fluroxypyr (110 g) | 4.8 | 2.5 | 1.0 | 0.0 |
| Fluroxypyr (100 g) + 0.025% Polymer | 5.0 | 2.3 | 1.2 | 0.0 |
| Fluroxypyr (50 g) | 5.0 | 3.2 | 2.0 | 0.3 |
| Fluroxypyr (50 g) + 0.025% Polymer | 4.8 | 3.0 | 1.0 | 0.3 |
| Fluroxypyr (25 g) | 5.0 | 4.3 | 2.0 | 0.2 |
| Fluroxypyr (25 g) + 0.025% Polymer | 5.0 | 3.7 | 1.5 | 0.0 |

TABLE 18

| Days after spraying | 7 | 14 | 21 | 28 |
|---|---|---|---|---|
| Control | 9.0 | 9.0 | 9.0 | 9.0 |
| Metsulfuron-methyl (3 g) | 7.0 | 5.5 | 4.5 | 3.3 |
| Metsulfuron-methyl (3 g) + 0.1% Polymer | 7.0 | 4.8 | 3.7 | 2.3 |
| Metsulfuron-methyl (1.5 g) | 7.0 | 5.3 | 5.0 | 3.5 |
| Metsulfuron-methyl (1.5 g) + 0.1% Polymer | 7.0 | 5.2 | 4.3 | 2.8 |

TABLE 19

| Days after spraying | 7 | 14 | 21 | 28 |
|---|---|---|---|---|
| Control | 9.0 | 9.0 | 9.0 | 9.0 |
| Metsulfuron-methyl (3 g) | 7.5 | 2.8 | 2.7 | 0.8 |
| Metsulfuron-methyl (3 g) + 0.1% Polymer | 7.3 | 2.5 | 2.2 | 0.5 |
| Metsulfuron-methyl (1.5 g) | 7.5 | 3.2 | 2.8 | 1.0 |
| Metsulfuron-methyl (1.5 g) + 0.1% Polymer | 7.2 | 3.0 | 2.3 | 0.5 |

EXAMPLE 16

A commercial formulation of the herbicide Isoproturon was diluted to give sprayable solutions containing various amounts of Isoproturon, with and without the same polymer as in Example 6.

The solutions were sprayed in a replicated field trial on to a commercial Winter Wheat crop (variety Riband) infester with A Myosurides (Blackgrass) in autumn following standard agricultural practice. No phytotoxicity to the wheat was observed with any treatment. The level of kill of Blackgrass was assessed visually.

The results are shown in Table 20.

TABLE 20

| Isoproturon g/ha | 0 | 1250 | 1250 | 1875 | 2500 |
|---|---|---|---|---|---|
| Polymer (%) | 0 | 0 | 0.1 | 0.1 | 0 |
| Blackgrass kill (%) | 0 | 88 | 90.5 | 95.0 | 95.0 |

Thus, at the lowest rate the polymer improves the performance of Isoproturon. A rate of 1875 g/ha isoproturon with polymer produces a kill achieved with 2500 g/ha in the absence of polymer.

EXAMPLE 17

This examples demonstrates the effect of changing the intrinsic viscosity of the polymer on spray angle.

Aqueous solutions were prepared containing known weights of (1) a non-ionic polyacrylamide having intrinsic viscosity (Iv) 2 dl/g, supplied as a 12.5% aqueous solution and (2) a non-ionic polyacrylamide having intrinsic viscosity (IV) 8 dl/g, supplied as a 50% inverse phase dispersion (typical of an anti-drift agent).

The solutions were sprayed through a Lurmark Flat Fan 04 80° Nozzle at a pressure of 3 bar, using an Azo Plot Sprayer. The nozzle was held at a known height over a bed of water-absorbent material. From the height of the nozzle and the length of the visible impression on the absorbent material, the spray angle could be calculated.

The results are shown in Table 21.

TABLE 21

| Polymer | Spray Angle (Degrees) | |
|---|---|---|
| Concentration (%) | Polymer IV2 | Polymer IV8 |
| 0 | 87.3 | 87.3 |
| 0.01 | 84.1 | 80.5 |
| 0.025 | 85.1 | 69.0 |
| 0.05 | 83.8 | 71.9 |
| 0.1 | 84.9 | 66.0 |
| 0.25 | 79.9 | — |
| 0.50 | 71.9 | — |

Thus the lower IV polymer causes substantially no distortion of the spray angle, especially at the concentrations that are preferred for use in the invention.

EXAMPLE 18

The composition being tested was sprayed on to winter barley (variety Igri) at the 2–3 leaf growth stage in trays of compost in a growing room. The leaves of the sprayed plant were subsequently cut down just above the growing point to remove any non-translocated glyphosate. The percentage kill and percentage re-growth were assessed after a defined period (3 days, 10 days or 14 days) after cutting the plant.

In each test, except for the controls (in which no active ingredient or polymer was sprayed) glyphosate was applied at a rage of 375 grams per hectare and polymer, if present, was applied at the rate of 150g dry polymer per hectare. The percentage kill and percentage re-growth were expressed as a percent of the kill and re-growth values respectively for the control, in each instance the number being the mean of 3 replicas. The polymers that were tested were as follows:

A) sodium polyacrylate intrinsic viscosity well below 1 dl/g supplied as a solution.

B) maleic anhydride/acrylic acid copolymer intrinsic viscosity below 1 dl/g supplied as a solution.

C) sodium polyacrylate intrinsic viscosity about 1 dl/g supplied as an aqueous solution.

E) substantially non-ionic polyacrylamide intrinsic viscosity about 3 dl/g as a 25% reverse phase dispersion (Similar to product D in Example 2).

F) substantially non-ionic polyacrylamide intrinsic viscosity below 1 dl/g introduced as a 12.5% aqueous solution.

G) copolymer of 70 acrylamide: 30 sodium acrylate intrinsic viscosity about 1 dl/g introduced as an aqueous solution.

H) Copolymer of 90 mole % acrylamide 10 mole % methylchloride quaternised dimethyl aminoethylacrylate intrinsic viscosity about 1–2 dl/g introduced as an aqueous solution.

I) copolymer of 90 mole % acrylamide 10 mole % methylchloridequaternised dimethyl aminoethylacrylate intrinsic viscosity about 3 dl/g introduced as an aqueous solution.

The results of one series of trials are shown in Table 22 below. The results of another series of trials are shown in Table 23 below.

TABLE 22

| | Assessment 3 days after cutting | | Assessment 10 days after cutting | |
|---|---|---|---|---|
| Product | % Re-growth | % Kill | % Re-growth | % Kill |
| Control | 100 | 0 | 100 | 0 |
| Glyphosate | 21.3 | 78.7 | 14.4 | 85.6 |
| Glyphosate + A | 22.0 | 78.0 | 13.9 | 86.1 |
| Glyphosate + B | 31.4 | 68.6 | 25.6 | 74.4 |
| Glyphosate + E | 5.6 | 94.4 | 2.6 | 97.4 |
| Glyphosate + F | 5.5 | 94.5 | 2.8 | 97.2 |

TABLE 23

| | 14 Days Post Treatment | |
|---|---|---|
| Product | % Re-growth | % Kill |
| 0 | 100 | 0 |
| Glyphosate | 25.7 | 74 |
| Glyphosate + C | 34 | 66 |
| Glyphosate + F | 19.1 | 81 |
| Glyphosate + G | 8.5 | 91 |
| Glyphosate + H | 16 | 84 |
| Glyphosate + I | 2.3 | 97.7 |

This data demonstrates that polymers that are free of acrylamide (polymers A, B and C) do not give the beneficial effect and that polymers that are substantially non-ionic polyacrylamide (D) and F)) or that are formed from monomers that contain a substantial amount of (more than 50%)

acrylamide with other monomers do give a beneficial effect on the efficacy of the active ingredient that is deposited on the plants.

EXAMPLE 19

The trial below was sited in a commercial crop of winter wheat (var. Riband). It was a randomised block trial with four replicates of each treatment. Plot dimensions were 2×10 m. The treatments were applied in a volume of water equivalent to 250 L/ha at a pressure of 3 bar, through Lurmark 02 Fl 10 flat fan nozzles.

The plant growth regulator, Chlormequat, was applied as a commercial formulation containing 700 g/l a.i. at rates of ½N, ⅔N, N and 2N (where N=normal rate of 2.3 L/ha) at Growth Stage 31, alone, and in combination with 2D (i.e., product D in Example 2) or 18F (i.e., product F of Example 18).

Just before harvest 20 straw lengths were selected from each plot at random and measured to assess the straw-shortening properties of the growth regulator/adjuvant combinations. The averaged results are shown below.

TABLE 24

| | STRAW LENGTHS (CM) | | |
|---|---|---|---|
| | | Adjuvant | |
| Chlormequat | NONE | 2D | 18F |
| 0 | 91.6 | — | — |
| ½N | 85.2 | 81.9 | 79.7 |
| ⅔N | 82.7 | 80.7 | 78.2 |
| N | 80.7 | 79.3 | 78.2 |
| 2N | 79.7 | | |

It can be seen that, at all dose levels use of 4291 or 5830 improved the performance of chlormequat. particular the two-third rate with either adjuvant, equalled or out-performed the normal rate of chlormequat alone.

EXAMPLE 20

Seed trays measuring 15×20 cm were half filled with damp potting soil and seeded with 0.5 g chickweed (Stellaria Media).

The seeds were covered with 1 cm potting compost and kept in darkness until germination.

Treatments of Duplosan New System CMPP (a commercial formulation containing 600 g/l of optically-active isomer mecoprop-P acid, as dimethylamine salt) were applied at rates equivalent to 0.5–1.5 l/ha, alone and in combination with 2D (0.1% of spray volume) or 18F (0.8% of spray volume).

The vistual percentage kill is shown in Table 25.

It is seen that in most cases, the use of an adjuvant improved the percentage kill, with 2D out-performing 18F.

TABLE 25

| Product Assessment | 1 Untreated Control | 2 Duplosan 0.50 L/ha | 6 Duplosan 0.05 L/ha 18F | 10 Duplosan 0.50 L/ha 2D | 3 Duplosan 0.75 L/ha | 7 Duplosan 0.75 L/ha 18F | 11 Duplosan 0.75 L/ha 2D |
|---|---|---|---|---|---|---|---|
| 6.8.92 2 week | 0 | 73 | 77 | 89 | 82 | 83 | 86 |
| 12.8.92 3 week | 0 | 78 | 75 | 88 | 81 | 79 | 88 |

| Product Assessment | 4 Duplosan 1.0 L/ha | 8 Duplosan 1.0 L/ha 18F | 12 Duplosan 1.0 L/ha 2D | 5 Duplosan 1.50 L/ha | 9 Duplosan 1.50 L/ha 18F | 13 Duplosan 1.50 L/ha 2D |
|---|---|---|---|---|---|---|
| 6.8.92 2 week | 83 | 85 | 87 | 85 | 89 | 87 |
| 12.8.92 3 week | 79 | 85 | 85 | 88 | 91 | 95 |

EXAMPLE 21

This trial was carried out to test the performance of two graminicides on blackgrass and volunteer barley in a crop of winter oil seed rape.

The trial was a four-replicate, randomised block, with plot sizes of 2 m×10 m.

The two herbicides used were "Laser" (200 g/l cycloxydim) and "Pilot" (500 g/l quizalofop-ethyl). Each were applied at normal (N) or half (½N) rates, alone, and with 5830 or 4291.

Application was made through a small plot sprayer, post-emergence.

Assessments 14 days after treatment showed no phytotoxicity to the Oil seed Rape.

Visual assessment of weed control was made 28 days after treatment. The results are shown below:

TABLE 26

| | Percentage Kill of Grass Weeds | | |
|---|---|---|---|
| Adjuvant | NONE | 2D | 18F |
| Cycloxydim | | | |
| 0 | 0 | — | — |
| ½N | 90 | 97 | 92.6 |
| N | 92 | 98 | 96 |
| Quizalofop-Ethyl | | | |
| 0 | | | |
| ½N | 75 | 81.7 | 75 |

TABLE 26-continued

| | Percentage Kill of Grass Weeds | | |
|---|---|---|---|
| Adjuvant | NONE | 2D | 18F |
| N | 81.7 | 87.3 | 78.3 |

2D significantly improved the performance of both herbicides. The half-rate with 2D was equal to or better than full-rate.

18F gave a small improvement with cycloxydim and had no benefit with quizalofop ethyl in this particular trial.

EXAMPLE 22

This trial was designed to measure the rate and efficacy of desiccation of potato haulms prior to harvest.

The trial was located in a commercial crop of ware potatoes, vat. Pentland Dell. The trial was designed as a randomised block with 3 replicates. Plot dimension was 2 m×10 m. Reglone a commercial formulation of Diquat (containing 200 g/l a.i.) was applied at normal and half-rate, with and without adjuvants.

The desiccation assessments were conducted using the following 0–9 scale.

| | Crop Desiccation Assessment Scale |
|---|---|
| Rating | Verbal Description |
| 0 | Crop completely dead |
| 1 | Crop nearly destroyed, but not all tissue dead |
| 2 | Some green tissue, but crop unlikely to make further growth |
| 3 | Very stunted, with dead and dying tissue, crop still making some growth |
| 4 | Marked inhibition of growth with more dying and dead tissue present |
| 5 | Readily distinguishable inhibition of growth with dying and dead tissue present |
| 6 | Reduced growth with initial signs that tissue is beginning to die |
| 7 | Severe discolouration with slight reduction in growth, and a degree of prostration |
| 8 | Slight discolouration and slight prostration |
| 9 | No reduction or injury, indistinguishable from the control |

The following table gives the desiccation assessments 7, 14 and 22 days post treatment. All readings are the mean of three replicates.

TABLE 27

| Treatment | 7 Days | 14 Days | (HARVEST) 22 DAYS |
|---|---|---|---|
| Reglone (N) | 4.0 | 1.5 | 1.3 |
| Reglone (N) + 2D (0.1%) | 4.0 | 1.2 | 1.3 |
| Reglone (N) + 18F (0.8%) | 4.0 | 2.0 | 1.0 |
| Reglone (½N) | 7.3 | 4.3 | 1.7 |
| Reglone (½N) + 2D (0.1%) | 5.3 | 2.5 | 1.6 |
| Reglone (½N) + 18F (0.8%) | 5.7 | 1.5 | 1.0 |
| Untreated Control | 8.0 | 6.0 | 5.0 |

Both adjuvants significantly improved the efficacy of Diquat applied at half rate.

EXAMPLE 22

Solutions of Round Up (glyphosate) were sprayed through a very fine nozzle at a rate of 1,5 L glyphosate/90 L water. The Volume Median Diameter and the number of particles below 104 μm were measured. The experiment was repeated in presence of 2D at 0.1% of spray volume, and at 0.8%.

The whole experiment was repeated through a fine nozzle with 1.5 L glyphosate/125 L water, The results are tabulated below.

| Nozzle Type | Formulation | VMD (μm) | % < 104 μm |
|---|---|---|---|
| Very fine | Glyphosate alone | 104 | 50.1 |
| (4110 10) | Glyphosate + 18F | 114 | 45.0 |
| 4 bar pressure | Glyphosate + 2D | 147 | 25.6 |
| Fine | Glyphosate alone | 162 | 25.4 |
| (4110 14) | Glyphosate + 18F | 156 | 27.9 |
| 2.0 bar pressure | Glyphosate + 2D | 171 | 18.2 |

It is seen that 2D significantly increases VMD and reduces the percentage droplets below 104 μm (the "driftable" droplets), whilst 18F has little effect.

EXAMPLE 23

Polymer X is a 50:50 copolymer of acrylamide and diallyldimethyl ammonium chloride, having IV2, supplied as an aqueous solution (8.5% solids).

The experiment was carried out in the growing room.

Barley plants (var. Marinka) were grown in trays to the ⅔ leaf stage and then sprayed with Round Up (a commercial formulation of glyphosate containing 360 g/l a.i.) at two different rates, with or without Polymer X at 0.1 % of the spray solution.

Plant Kill was assessed visually at 14, 21 and 26 days. The results are shown below.

TABLE 28

| | Percentage Kill | | |
|---|---|---|---|
| Treatment | 14 Day | 21 Day | 26 Day |
| Glyphosate 0.75 L/ha | 71.7 | 75 | 78 |
| Glyphosate 0.75 L + Polymer X | 78.7 | 76 | 86 |
| Glyphosate 1 L/ha | 78.7 | 82 | 92 |
| Glyphosate 1 L + Polymer X | 82.7 | 91 | 97 |

Thus Polymer X increased the kill with glyphosate at both dose rates.

I claim:

1. A process comprising providing a reverse phase emulsion in oil of a water soluble polymer which has intrinsic viscosity at least 4 dl/g and which is formed of 51 to 100% acrylamide and 0 to 49% ethylenically unsaturated monomer selected from anionic and cationic monomers, dispersing this emulsion in an aqueous phase and thereby forming an emulsion of the oil as particles which have a weight average particle size of below 25 μm in a solution of the polymer, incorporating a foliar systemic active ingredient in the aqueous phase before or after dispersing the reverse phase emulsion into the aqueous phase and thereby forming a dilute sprayable composition containing the active ingredient and a solution of the polymer with the oil emulsified therein having a weight average particle size of below 25 µm, and spraying the composition on to leaves of plants.

2. A process according to claim 1 in which said weight average particle size is below 10 µm.

3. A process according to claim 1 in which a number average particle size is within 30% of said weight average particle size.

4. A process according to claim 1 in which the sprayable composition contains 0.005 to 0.5% by weight of the polymer.

5. A process according to claim 1 in which the sprayable composition contains 0.1 to 5% by weight of the active ingredient.

6. A process according to claim 1 in which the polymer is a polymer of 97 to 100% by weight acrylamide and 0 to 3% by weight sodium acrylate.

7. A process according to claim 1 in which the polymer is a polymer of 80 to 100% by weight acrylamide and 0 to 20% by weight anionic ethylenically unsaturated monomer.

8. A process according to claim 1 in which the active ingredient is a plant growth regulator or a herbicide.

9. A process according to claim 1 comprising the preliminary step of providing the polymer as a reverse phase emulsion and dissolving the polymer in water to form a solution of the polymer.

10. A process according to claim 9 in which the solution a solution of the polymer of the polymer is formed and the solution is then mixed with the active ingredient.

11. A process according to claim 9 in which the polymer has intrinsic viscosity 4 to 15 dl/g.

12. A process according to claim 9 in which the polymer has intrinsic viscosity 4 to 15 dl/g, the polymer is provided as a reverse phase emulsion in water, the polymer is dissolved in water by mixing the emulsion with the water, and the resultant solution is then blended with active ingredient.

13. A process according to claim 1 in which the active ingredient is selected from glyphosate, chlormequat, diquat, chlorpyrilid and hormone weedkillers.

* * * * *